(12) United States Patent
Mills

(10) Patent No.: US 7,179,280 B2
(45) Date of Patent: *Feb. 20, 2007

(54) THERMAL DEVICE

(76) Inventor: Matthew Mills, 2103 Ventura Blvd., Suite 703, Woodland Hills, CA (US) 91364

( * ) Notice: Subject to any disclaimer, the term of this patent is extended or adjusted under 35 U.S.C. 154(b) by 0 days.

This patent is subject to a terminal disclaimer.

(21) Appl. No.: 10/774,707

(22) Filed: Feb. 9, 2004

(65) Prior Publication Data

US 2005/0177216 A1   Aug. 11, 2005

(51) Int. Cl.
*A61F 7/00* (2006.01)
(52) U.S. Cl. ...................................... 607/108; 607/114
(58) Field of Classification Search ........ 607/108–112, 607/114; 5/951
See application file for complete search history.

(56) References Cited

U.S. PATENT DOCUMENTS

| D336,339 | S | 6/1993 | Pryor | D24/207 |
| 5,300,104 | A | 4/1994 | Gaudreault et al. | 607/114 |
| 5,476,492 | A | 12/1995 | Unrug | 607/114 |
| D369,218 | S | 4/1996 | Vandenbelt | D24/206 |
| D372,984 | S | 8/1996 | Jordan | D24/206 |
| 5,571,155 | A | 11/1996 | Bastille | 607/114 |
| 5,603,727 | A | 2/1997 | Clark et al. | 607/108 |
| 5,890,487 | A | 4/1999 | Kimmel | 128/845 |
| 5,948,010 | A * | 9/1999 | Adamec | 607/96 |
| D442,285 | S | 5/2001 | Perry | D24/206 |
| 6,336,935 | B1 * | 1/2002 | Davis et al. | 607/112 |
| 6,383,053 | B1 * | 5/2002 | Segers | 446/386 |
| 6,796,996 | B2 * | 9/2004 | Antinoro | 607/114 |
| 2002/0193857 | A1 | 12/2002 | Lavine | 607/114 |

FOREIGN PATENT DOCUMENTS

WO    WO 01/78797    10/2001 .................... 15/18

* cited by examiner

*Primary Examiner*—Linda C. M. Dvorak
*Assistant Examiner*—Aaron Roane
(74) *Attorney, Agent, or Firm*—Cislo & Thomas LLP

(57) ABSTRACT

Provided is a thermal device for applying thermal energy to the body of a person, animal, or other surface including segmented organic filler.

10 Claims, 3 Drawing Sheets

THERMAL DEVICE

BACKGROUND

Heating pads have been used for years to warm the body during cold weather and to help soothe sore muscles or joints after heavy work or exercise. Ice has also been used as a way of preventing inflammation and swelling of injured areas of a body. Recent developments in gel technology may have produced a gel pack that can be heated in a microwave oven, or cooled in a freezer. This type of pack, however, may have to be wrapped in a towel before use, as direct contact with the skin can cause injury to the user. Moreover, the gel packs do not provide lasting heat. Finally, the gel packs may crack or break open. Once the plastic container has failed, the gel pack is useless as the gel cannot be contained.

Besides gel packs, traditional heating pads may also be available. These pads are typically powered by electricity and are not portable. Moreover, these pads cannot be chilled to provide cold therapy if such therapy is needed.

Furthermore, some packs may utilize grains as filler for heating devices. This type of filler may have drawbacks including the grain popping, cracking, and molding. This type of pack may be difficult to clean and may begin to emit odors after repeated use.

What is needed is an organic filler for a washable pack that resists popping, cracking, and molding.

SUMMARY

Provided is a thermal device for applying thermal energy to the body of a person, animal, or other surface including segmented organic filler.

DETAILED DESCRIPTION

The detailed description set forth below in connection with the appended drawings is intended as a description of exemplary embodiments of the invention and is not intended to represent the only forms in which the present invention may be constructed and/or utilized. The description sets forth the functions and the sequence for constructing and operating the invention in connection with the illustrated embodiments. However, it is to be understood that the same or equivalent functions and sequences may be accomplished by different embodiments that are also intended to be encompassed within the spirit and scope of the invention.

Figure 1:
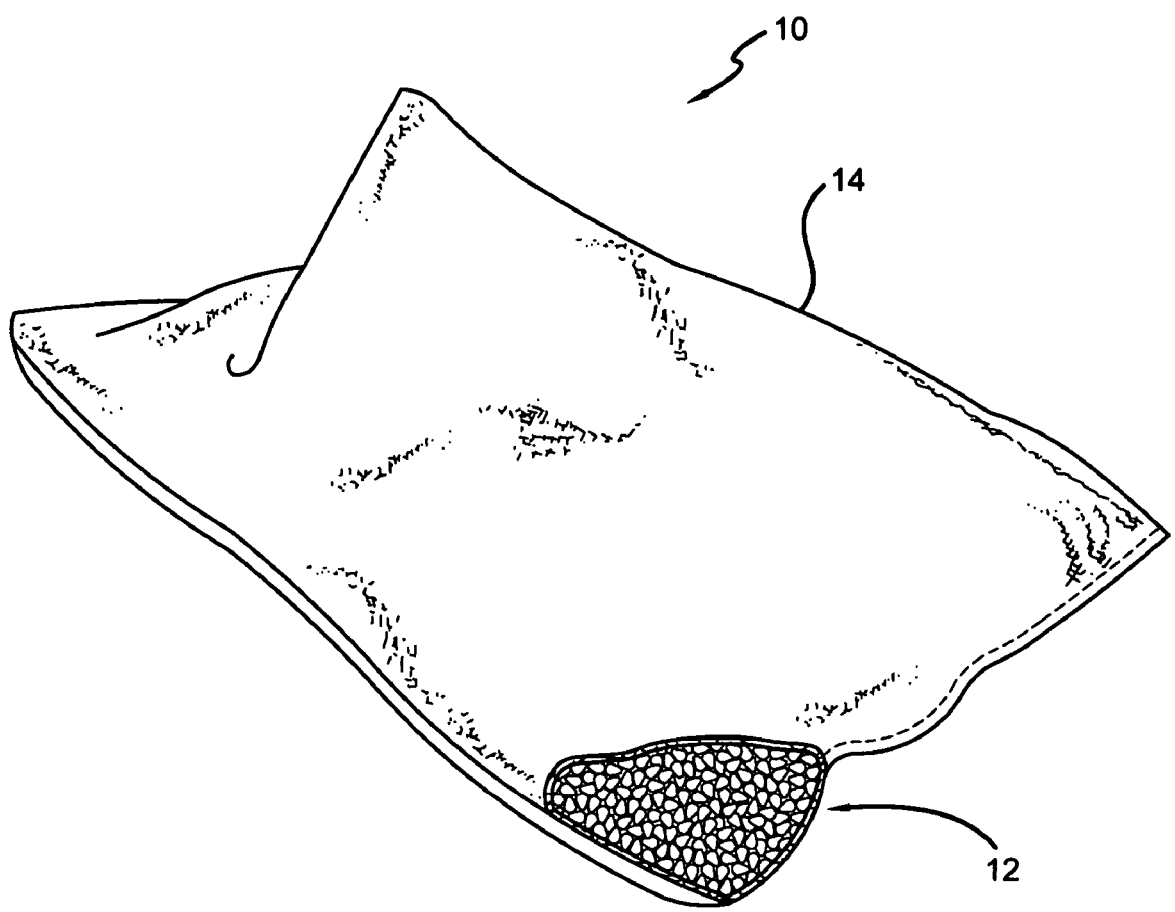
FIG. 1 is perspective, cut-away view of an exemplary embodiment of a thermal aid.

FIG. 1 shows an exemplary embodiment of a thermal device, generally at 10. System 10 may include filler 12 which may be enclosed by an enclosure or receptacle 14. Filler 12 may be organic such as different types of grain. Furthermore filler 12 may be segmented such that particular portions of the grain are removed. Filler 12 may be a degermed grain, such as corn, which may be also organically grown, or other type of grain, as desired. Furthermore, filler 12 may be an embryo free grain, such as embryo free corn. Additionally, filler 12 may be a dissected grain, such as corn, and also may be kiln or oven dried to impart properties to alter the thermal characteristics of filler 12.

Receptacle or container 12 may be made of a cotton material, nylon, plastics, and other fabric and material, as desired. The thermal device may be used by imparting thermal energy upon it. Thermal energy may be imparted upon the thermal device 10, via a microwave oven, or other heating methods, such that the thermal device will accept thermal energy and may retain it for a relatively long period of time. In this manner, the thermal device may have thermal energy added to it via a microwave, oven, or other methods, and may not dissipate that heat rapidly, such that the device may be used to impart thermal energy to the body of a person, animal, or other surface as desired.

The filler may be degermed, kiln or oven dried corn such that it will resist popping, cracking, and molding when used repeatedly. Allergic diseases that are caused or exacerbated by mold and fungi may be the most prevalent and common conditions treated by physicians. Molds may be responsible for allergic reactions and most notably that involving the respiratory system. Utilizing segmented grain may reduce the amount of mold caused by use of the thermal device, thereby reducing allergic reactions and limiting the effects of the thermal device to thermal energy transfer to the person, animal, or other surface.

In one embodiment filler 12 is degermed, kiln or oven dried corn. Because the germ has a greater percentage of oil and water, removing it may reduce the chance of the corn popping. Furthermore, this type of corn may decrease the likely hood of cracking when in use. Yet further, the reduced cracking may reduce the amount of mold and fungi formed within the cracks and/or on the filler 12. This may result in the thermal device 10 not acquiring odors after repeated use. Furthermore, it may also allow for the device to be cleaned without causing degradation, molding, or fungus growing on the filler 12 and/or the device 10. Filler 12 may also be organically grown grain, such as corn, wheat, oats, barley, etc., and the like.

Segmenting of the grain may include separating distinct portions of the kernel. Furthermore these segments may be separated to yield desired elements for use in the device. The segmenting of the grain may include a dry milling process to remove the bran coat and germ from the grain kernel while keeping the endosperm portion largely intact. This process may yield prime products which are high in starch, low in oil, and essentially free of bran and germ and which may have an excellent shelf life and stability. Segmenting may also include dissecting the grain, and/or removing the embryo of the grain.

The filler 12 may be kiln or oven at around 150°–220° F. This drying may continue until the moisture level of the filler 12 is generally in a range of 8%–15%. With this low moisture level mold and fungi may be reduced and may not be formed.

Kiln or oven drying may also prevent the desired product from rehydrating during use. Therefore, after the device 10 may get wet with water or other liquids it may then dry naturally and will tend to return to a level at which the moisture content is very near to the moisture level of the grain after the drying process. With this configuration the thermal device 10 may be a natural product that may be cleaned with soap and water without causing mold and fungus to grow in/or filler 12 and system 10.

With this configuration, the thermal device may be utilized to treat ailments such as, but not limited to, arthritis, back pain, fibromyalgia, sprains/strains, ear aches, migraines/headaches, bee stings, muscle soreness, menstrual cramps, multiple sclerosis, babies with colic, lactation enhancement in pregnant women, growing pains/leg cramps, insomnia, sports injuries, neck pain, carpel tunnel syndrome, influenza, fever, sunburn, nose bleeds, and ischium sciatic nerve.

Furthermore, thermal energy in the form of cold may be added to the system, also. Thermal device 10 may be placed in a freezer to impart thermal energy upon the device 10. Again the device will dissipate the thermal energy relatively slowly such that the device may be used for a cold pack, as well as a heat pad as described above. Furthermore, other devices and processes may be utilized to impart cold thermal energy to the device, as desired.

In this manner, the device may be utilized for sports injuries both as a hot and cold pack, while reducing the amount of mold and fungus that may form in or on filler 12 or device 10. This device may exhibit better thermal characteristics than current plastic or chemical based packs. Furthermore, this device may be reused multiple times thereby reducing costs of replacement, among others.

Figure 2:
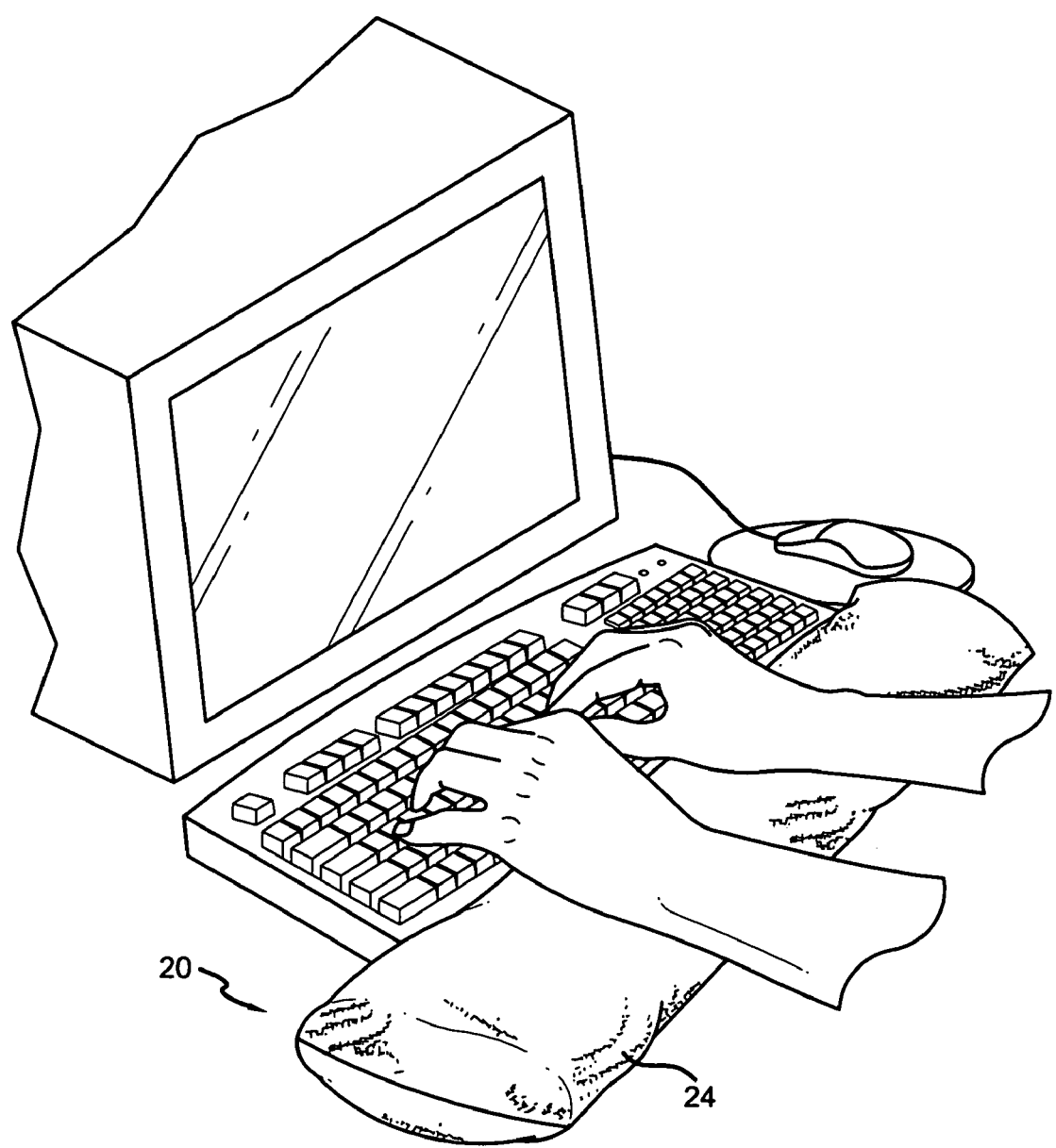
FIG. 2 is a perspective view of a thermal aid according to another exemplary embodiment.

FIG. 2 shows another exemplary embodiment of the present invention generally at 20. Device 20 may be configured to be placed in front of a computer keyboard, such that a user may rest their wrists upon it. With this configuration hot or cold thermal energy may be applied to the wrists of the user, which may reduce the pain or incidents of carpel tunnel syndrome, among other ailments. This embodiment may also include an enclosure or receptacle 24 in a different configuration than shown in FIG. 1. It will be appreciated that many different materials and configurations are contemplated by this application. Furthermore many different materials and configurations may be utilized for the enclosure, as desired.

All thermal devices described herein may have the ability to be cleaned with soap and water, by washing under warm water with antibacterial or dish soap, and then allowed to dry naturally. With this configuration the devices may be utilized for hot and cold compresses and may have more enhanced characteristics than those currently available.

Figure 3:
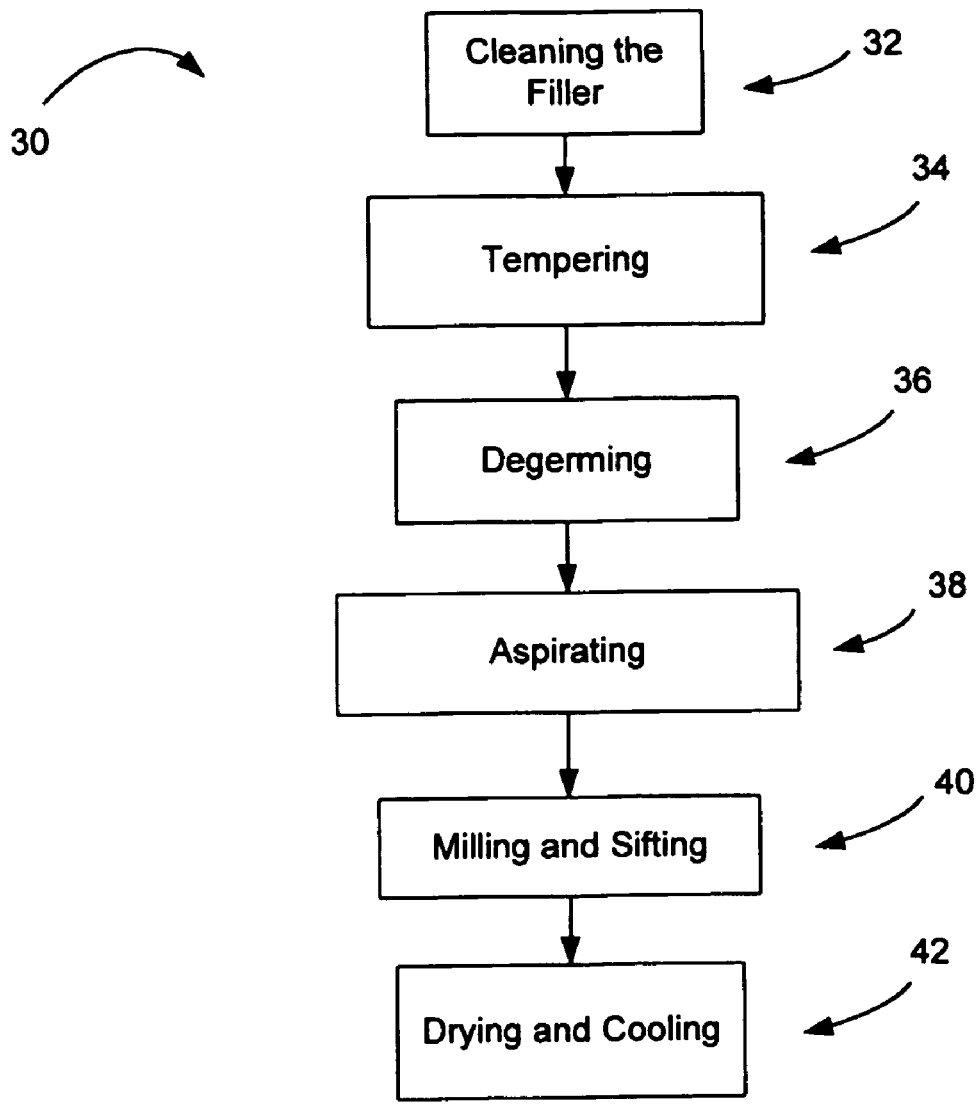
FIG. 3 is a block diagram of a method according to an exemplary embodiment.

A method of segmenting grain is shown in FIG. 3, generally at 30. This process may include cleaning the grain, at 32, in which size and density differences are utilized to separate broken kernels, foreign materials, and undesirable kernels or grain from the desired whole kernels or grain prior to milling.

This process may also include tempering, at 34, in which clean kernels or grain may be moistened or tempered to loosen and toughen the bran coat and/or soften the germ or embryo to facilitate separation in a degerminator.

This process may also include degermination, at 36, in which the initial separation into the component parts may begin in the degerminator. A specifically configured attrition mill containing a truncated core, surfaced with numerous purling knobs, may rotate inside of a perforated housing. As the tempered kernels or grain pass through this device, the abrading action may peel the bran coat and germ or embryo away from the endosperm. The germ or embryo, hull, and small endosperm pieces may pass through the perforation in the housing and the larger endosperm pieces may exit the end, or tail, of the germinator.

This process may also include aspiration, at 38, in which additional bran and light germ pieces are aspirated from the endosperm to further enhance the initial separation to separate out undesirable elements.

This process may further include milling and sifting of the desired elements, at 40. This portion of the process may remove additional germ or embryo particles and only retain the clean endosperm pieces that are of a desired size and desired granulation.

This process may also include drying and cooling, at 42, which may reduce the moisture content of the desired elements in desired product ranges. This drying process may be accomplished by a kiln, oven, or other device, or by natural drying, as desired.

In closing, it is to be understood that the exemplary embodiments described herein are illustrative of the principles of the present invention. Other modifications that may be employed are within the scope of the invention. Thus, by way of example, but not of limitation, alternative configurations may be utilized in accordance with the teachings herein. Accordingly, the drawings and description are illustrative and not meant to be a limitation thereof.

What is claimed is:

1. A thermal device for applying thermal energy to the body of a person, animal or other surface, comprising:
   degermed corn disposed substantially in individual kernel form to have a moisture content within approximately 8%–approximately 15%, said moisture content facilitating reheating of said degermed corn; and
   an enclosure configured to enclose a plurality of said degermed corn kernels to be displaceable one relative to the other therewithin.

2. The thermal device of claim 1, wherein said enclosure is made from fabric.

3. The thermal device of claim 1, wherein said degermed corn is kiln dried.

4. The thermal device of claim 1, wherein said degermed corn is oven dried.

5. The thermal device of claim 1, wherein said enclosure is generally rectangular.

6. A thermal device for applying thermal energy to the body of a person, animal or other surface, comprising a thermal filler contained within an enclosure including degermed corn formed by a plurality of individual kernels to have a moisture content within approximately 8%–approximately 15%, said moisture content facilitating reheating of said degermed corn, said degermed corn configured to accept thermal energy.

7. A thermal device for applying thermal energy to the body of a person, animal or other surface, comprising:
   degermed corn disposed substantially in individual kernel form to have a moisture content within approximately 8%–approximately 15% said moisture content facilitating reheating of said degermed corn; and
   a receptacle configured to enclose a plurality of said degermed corn kernels, said degermed corn kernels being displaceable one relative to the other within said receptacle.

8. The thermal aid of claim 7, wherein said degermed corn is kiln-dried grain.

9. The thermal device of claim 7, wherein said degermed corn is oven dried.

10. The thermal device of claim 7, wherein receptacle is generally rectangular.

* * * * *